(12) United States Patent
Paz et al.

(10) Patent No.: US 8,357,173 B2
(45) Date of Patent: Jan. 22, 2013

(54) ANASTOMOSIS DEVICE

(75) Inventors: Ronen Paz, Nirit (IL); Yoav Heichal, Ganey Yehuda (IL)

(73) Assignee: SeamVad Ltd. (IL)

( * ) Notice: Subject to any disclaimer, the term of this patent is extended or adjusted under 35 U.S.C. 154(b) by 236 days.

(21) Appl. No.: 12/994,987

(22) PCT Filed: May 31, 2009

(86) PCT No.: PCT/IL2009/000535
§ 371 (c)(1),
(2), (4) Date: Nov. 29, 2010

(87) PCT Pub. No.: WO2009/144728
PCT Pub. Date: Dec. 3, 2009

(65) Prior Publication Data
US 2011/0087253 A1 Apr. 14, 2011

Related U.S. Application Data

(60) Provisional application No. 61/071,962, filed on May 28, 2008.

(51) Int. Cl.
*A61B 17/04* (2006.01)
(52) U.S. Cl. ........................................ 606/153; 606/151
(58) Field of Classification Search ........................ None
See application file for complete search history.

(56) References Cited

U.S. PATENT DOCUMENTS

| | | | |
|---|---|---|---|
| 3,774,615 A | 11/1973 | Lim et al. | |
| 4,214,586 A * | 7/1980 | Mericle | 606/154 |
| 4,470,415 A | 9/1984 | Wozniak | |
| 5,586,987 A | 12/1996 | Fahy | |
| 5,797,951 A * | 8/1998 | Mueller | 606/198 |
| 6,036,704 A * | 3/2000 | Yoon | 606/153 |
| 6,312,443 B1 * | 11/2001 | Stone | 606/198 |
| 7,955,342 B2 * | 6/2011 | Redha et al. | 606/153 |
| 7,998,155 B2 * | 8/2011 | Manzo | 606/155 |
| 2001/0001827 A1 | 5/2001 | Chapman | |
| 2005/0192602 A1 | 9/2005 | Manzo | |
| 2005/0228411 A1 * | 10/2005 | Manzo | 606/153 |

FOREIGN PATENT DOCUMENTS

| | | |
|---|---|---|
| WO | 9629939 A1 | 10/1996 |
| WO | 02096299 | 12/2002 |
| WO | 04000093 A2 | 12/2003 |

OTHER PUBLICATIONS

International Search Report and Written Opinion, PCT/IL2009/000535, dated Oct. 7, 2009.
Jackson et al., TCM, 10(5); 192-197 (2000).

* cited by examiner

*Primary Examiner* — Corrine M McDermott
*Assistant Examiner* — Todd J Scherbel
(74) *Attorney, Agent, or Firm* — Lerner, David, Littenberg, Krumholz & Mentlik, LLP

(57) ABSTRACT

An anastomosis device (11) for use in coupling two ends of tubular stumps (13). The device comprises two hollow tubular members (21), adapted to be placed over said tubular stumps. The hollow tubular members are further capable of radially expanding from a first inner diameter to a second, larger inner diameter. Each hollow tubular member, while having the first inner diameter, being further adapted to allow everting of the stump proximal end over the tubular member proximal end. The device further comprises an elastic sleeve (31), adapted to be put on said tubular member proximal ends with the everted ends of said stumps, the sleeve further being adaptable to maintain said everted ends in a predetermined distance.

14 Claims, 7 Drawing Sheets

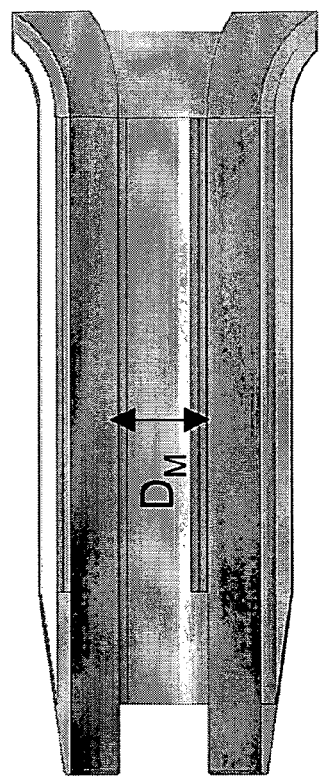
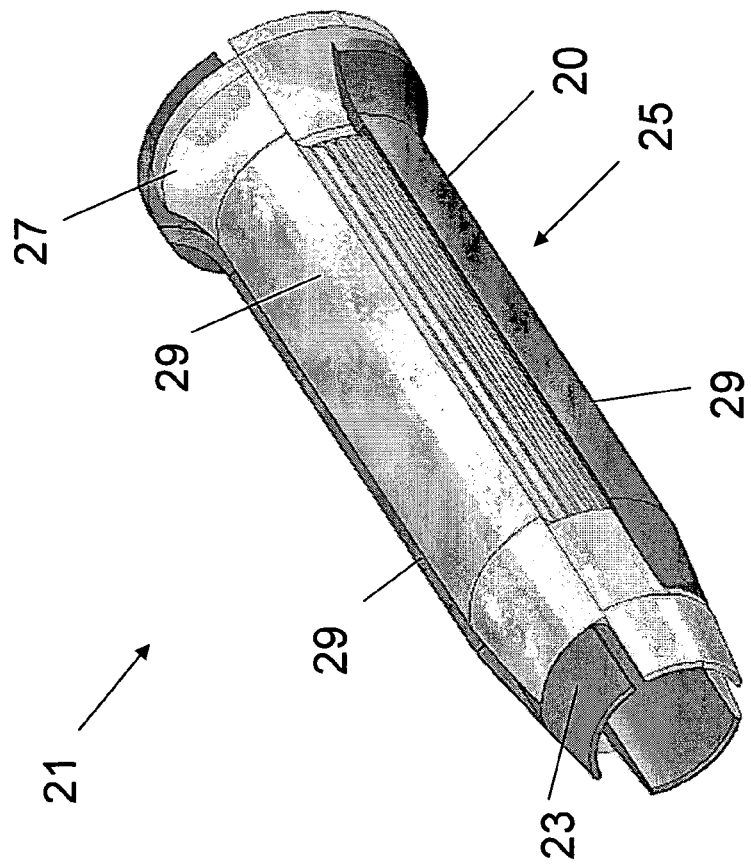
Fig. 2B
Fig. 2A

ANASTOMOSIS DEVICE

CROSS-REFERENCE TO RELATED APPLICATIONS

This application is a national phase entry under 35 U.S.C. §371 of International Application No. PCT/IL2009/000535, filed May 31, 2009, published in English, which claims the benefit of the filing date of U.S. Provisional Patent Application No. 61/071,962, filed on May 28, 2008, the disclosures of which are incorporated herein by reference.

FIELD OF THE INVENTION

This invention relates to a device and a method for end-to-end anastomosis of tubular structures.

BACKGROUND OF THE INVENTION

An anastomosis is an operative union of two hollow or tubular structures. Anastomotic structures can be part of a variety of systems, such as the vascular system, the digestive system, or the genitourinary system. An anastomosis is termed end-to-end when the terminal portions of tubular structures are anastomosed.

A wide variety of anastomosis devices and methods have been developed for anastomosing ends of living vessels. End-to-end anastomosis may be accomplished either by suturing, stapling or mechanical coupling. Suturing is generally difficult to perform, especially when very small vessels are involved, and requires great skill and experience on the part of the surgeon. Stapling and mechanical coupling of blood vessels has been suggested to avoid the disadvantages of suturing, and to provide a faster, more reliable and relatively simple method of anastomosis.

U.S. Pat. No. 4,214,586 discloses a three-piece anastomotic coupling device for end-to-end anastomosis of tubular members consisting of two open bore cylindrical adaptors and an open bore cylindrical connector. Each end of a tubular member is passed through the axial bore of an adaptor and everted over the end thereof. The adaptors are then inserted into opposite ends of the connector until the everted ends of the vessel abut under light compression. Integral locking means are provided to secure the adaptors and tubular members of the connector piece.

U.S. Pat. No. 4,470,415 discloses a means and method for sutureless surgical anastomosis. A heat shrinkable sleeve is placed around two tubular members to be anastomosed and then shrunk to engage and maintain the two tubular members in an anastomotic relationship. The ends of the tubular members are everted over rigid or semi-rigid ferrules placed on the ends of the tubular members.

SUMMARY OF THE INVENTION

In accordance with one aspect of the present invention there is provided a device for anastomosis of a first and a second tubular stumps, each having a stump proximal end, each of said tubular stumps further having a shrunk outer diameter in their shrunk state and an expanded outer diameter in their expanded state. The device comprises a first and a second hollow tubular member, adapted to be placed over said first and second stumps, respectively. Each hollow tubular member has a tubular member proximal end, a tubular member middle section, a first inner diameter, which is at least equal to said shrunk outer diameter, and a second inner diameter, which is at least equal to said expanded outer diameter. The hollow tubular members are further capable of radially expanding from said first inner diameter to said second inner diameter. Each hollow tubular member, while having the first inner diameter, being further adapted to allow everting of the stump proximal end over the tubular member proximal end. The device further comprises an elastic sleeve having two sleeve ends, adapted to be put on said tubular member proximal ends with the everted ends of said stumps, the sleeve further being adaptable to maintain said everted ends in a predetermined distance.

The hollow tubular members are adapted to be expanded due to an expansion of said stumps from said shrunk state to said expanded state, and may be expanded to at least twice its original diameter. The hollow tubular members may comprise at least two segments, each segment partially overlapping with its neighboring segments, to create a diameter at least equal to said first inner diameter, and may further comprise restraining means for preventing it from having a diameter less than said first inner diameter, once the hollow tubular member is placed over said stump. Alternatively, the hollow tubular members may be prepared as a single body made of, for example, plastic polymer or metal allow.

The hollow tubular members may be expanded by a ratchet mechanism, a saw tooth mechanism, by means of spring or any other mechanism capable of expanding them to a desired diameter.

The hollow tubular members may further be X-ray, ultrasound or Doppler transparent and may be used with imaging techniques such as for example Computerized Tomography (CT), Magnetic Resonance Imaging (MRI) or Isotopic Scanning.

The elastic sleeve may further have at least one holding means for maintaining said everted ends in said distance, and is further adapted to cover the everted ends of the stumps and at least a part of the middle sections of the hollow tubular members.

The predetermined distance between the everted ends of the stumps is chosen so as to provide maximal healing. The distance may be in a range of 0 to about 5 mm, more particularly, in a range of about 0.5 mm to about 3 mm, more particularly about 2 mm. The term "about" in the context of the present invention means +/−10% of the defined value. In one embodiment the distance is equal to zero (i.e. whereby the everted ends of the stumps are in contact with each other). Specifically, when the hollow tubular members are blood vessels, the distance between the everted ends allows the formation of a blood clot, which serves as a natural substrate for regeneration of the blood vessel wall. Without wishing to be bound by theory, allowing a space for generation of a blood clot mimics the natural course of events which occur following rupture of a blood vessel. Blood platelets play a key role in maintaining the integrity of the vascular system through their ability to arrest bleeding (haemostasis) and promote repair of injured blood vessels (Jackson et al., Trends Cardiovasc Med. 2000 July; 10(5):192-7). The rupture of a blood vessel initiates a clotting procedure which initially prevents blood loss and subsequently provides both an infrastructure as well as suitable stimulants for gradual formation of blood vessel wall tissue, including the intima, media and serosa (adventitia).

The device may further comprise an applicator capable of at least placing the hollow tubular members over the stumps.

The device may further be drug eluting.

According to another aspect of the present invention, there is provided a hollow tubular member adapted to be placed over a stump having a stump proximal end, a shrunk outer diameter in its shrunk state, and an expanded outer diameter in its expanded state. The hollow tubular member comprises a tubular member proximal end, a tubular member middle section, a first inner diameter, which is at least equal to said shrunk outer diameter, and a second inner diameter, which is at least equal to said expanded outer diameter. The hollow tubular member is further capable of radially expanding from said first inner diameter to said second inner diameter, each hollow tubular member, while having the first inner diameter, being further adapted to allow everting of the stump proximal end over the tubular member proximal end.

According to another aspect of the present invention, there is provided a method of performing an anastomosis of a first and a second tubular stumps, each having a stump proximal end, and further having a shrunk outer diameter in its shrunk state and an expanded outer diameter in its expanded state, the method comprising:
  providing a device comprising a first and a second hollow tubular members, each having a tubular member proximal end, a tubular member middle section, a first inner diameter, which is at least equal to said shrunk outer diameter, and a second inner diameter, which is at least equal to said expanded outer diameter, said hollow tubular members further being capable of radially expanding from said first inner diameter to said second inner diameter; and an elastic sleeve having two sleeve ends;
  determining first inner diameter of the hollow tubular members;
  placing the first hollow tubular member over the first stump, while it is in its shrunk state;
  placing the second hollow tubular member over the second stump, while it is in its shrunk state;
  everting the proximal ends of the first and second stumps over the proximal ends of the first and second hollow tubular members, respectively;
  putting the sleeve ends on the corresponding proximal ends of the hollow tubular members with the everted proximal ends of the stumps; and
  maintaining the everted proximal ends of the stumps in a predetermined distance from each other.

BRIEF DESCRIPTION OF THE DRAWINGS

In order to understand the invention and to see how it may be carried out in practice, embodiments will now be described, by way of non-limiting example only, with reference to the accompanying drawings, in which:

FIG. 2A is a schematic perspective view a hollow tubular member constituting a part of the device shown in FIG. 1;

FIG. 2B is a schematic front view a hollow tubular member constituting a part of the device shown in FIG. 1;

DETAILED DESCRIPTION OF EMBODIMENTS

Figure 1A:
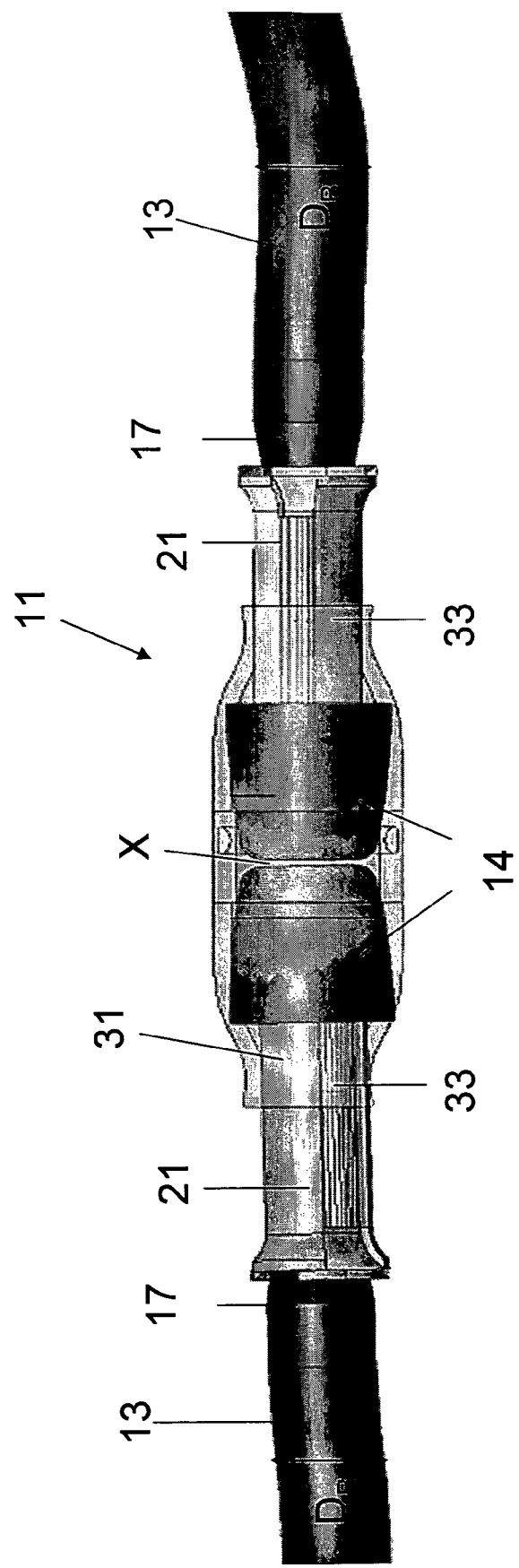
FIGS. 1A and 1B schematically illustrate a device according to the present invention, with its tubular members in a partially shrunken and final expanded state, respectively
Figure 4:
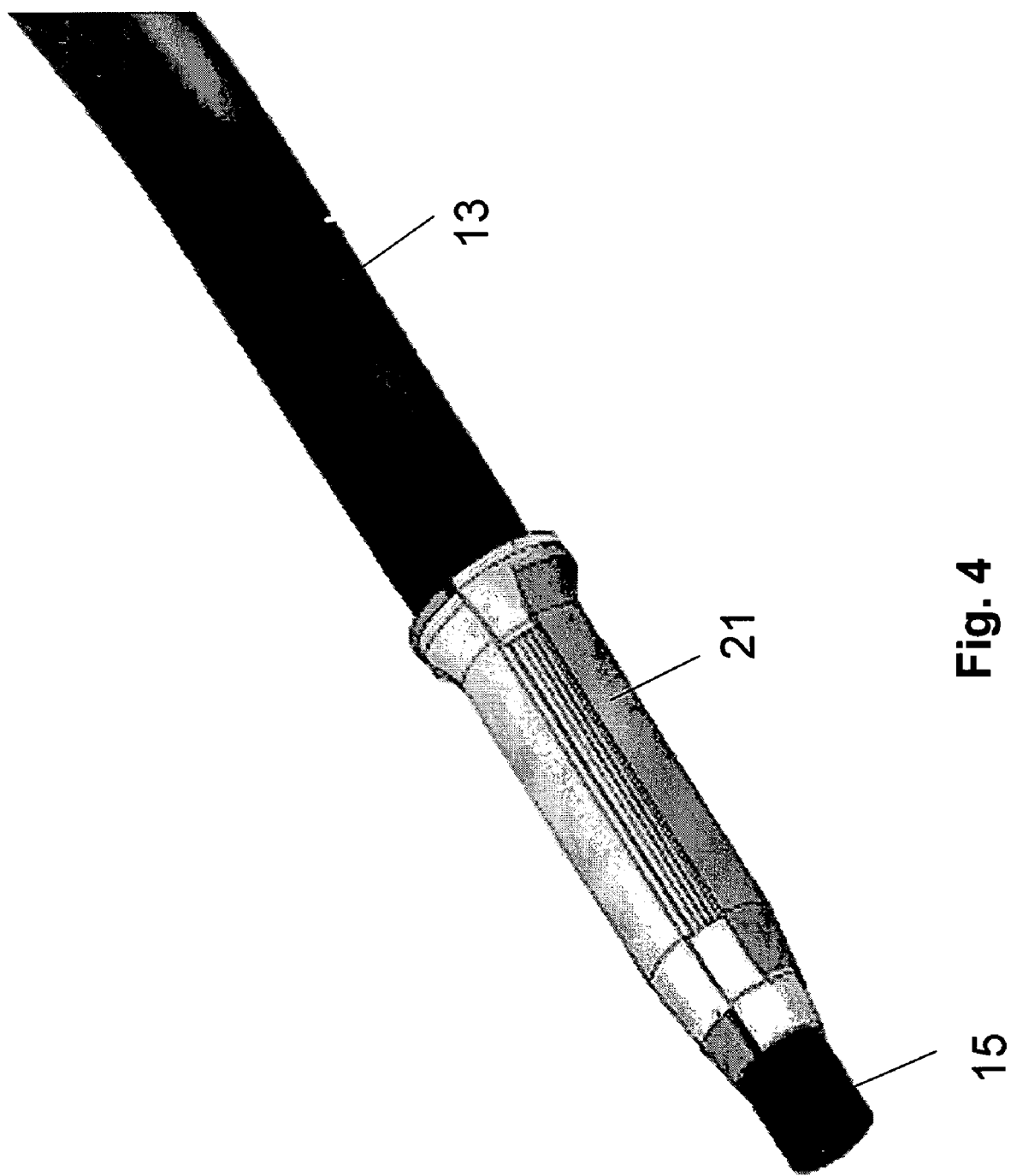
FIG. 4 is a schematic illustration of the hollow tubular member shown in FIGS. 2, 3A and 3B, put over a blood vessel.
Figure 5B:
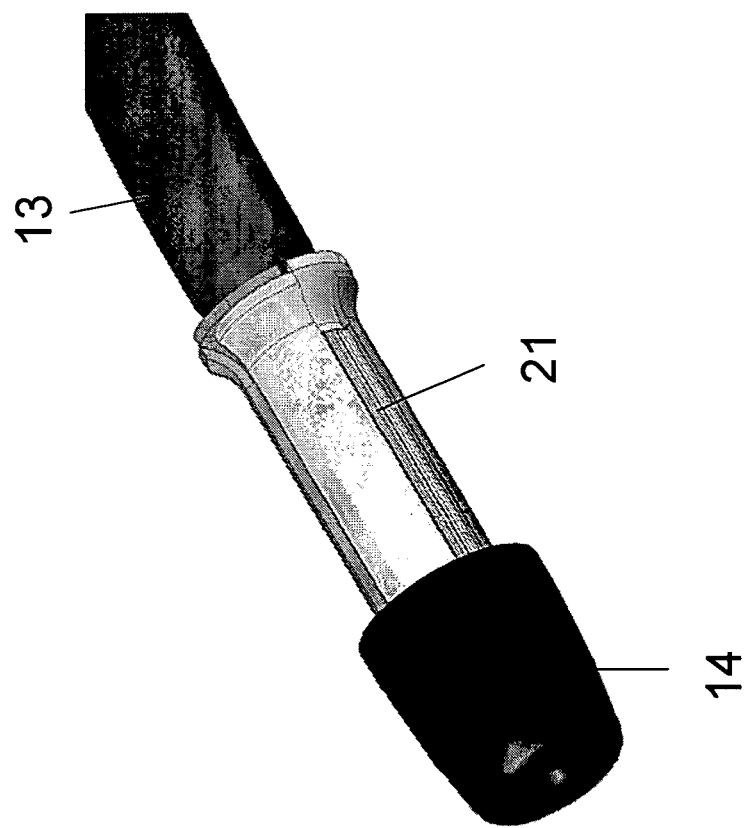
FIGS. 5A and 5B schematically show an everting process according to the present invention.
Figure 5A:
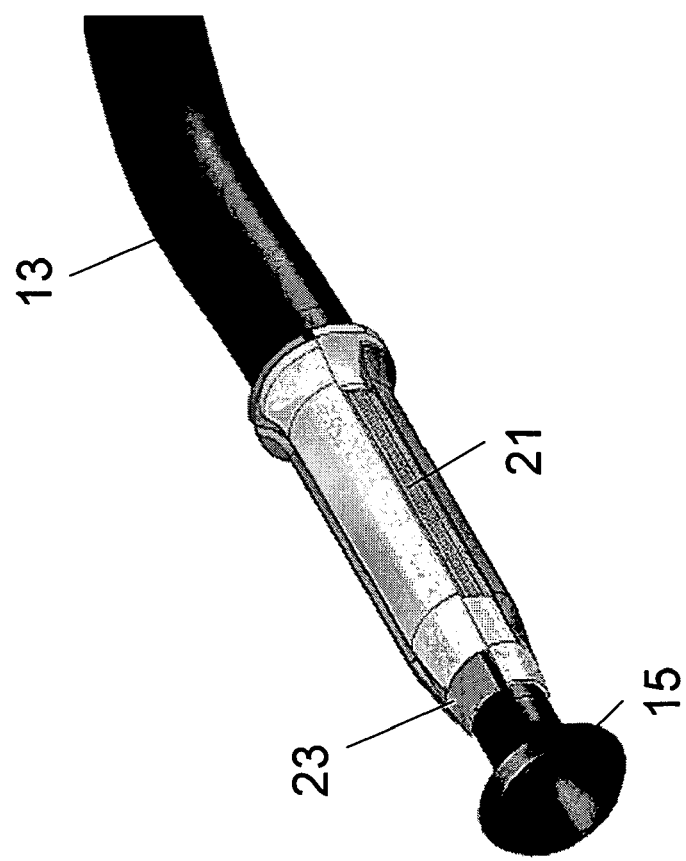

FIG. 1A illustrates a device generally designated 11 for anastomosis of two blood vessels 13 having proximal ends 15 (shown in FIGS. 4 and 5A). The device 11 comprises two hollow tubular members 21, described below, and an elastic sleeve 31 having two ends 33. The blood vessels have an outer diameter $D_B$, which may vary according to a state of the blood vessel 13. In its shrunk state the blood vessel 13 has a shrunk diameter, so that $D_B=D_{SH}$ and in its expanded state the blood vessel 13 has an expanded diameter, so that $D_B=D_{EX}$, i.e. $D_{SH} \leq D_B \leq D_{EX}$.

Figure 3:
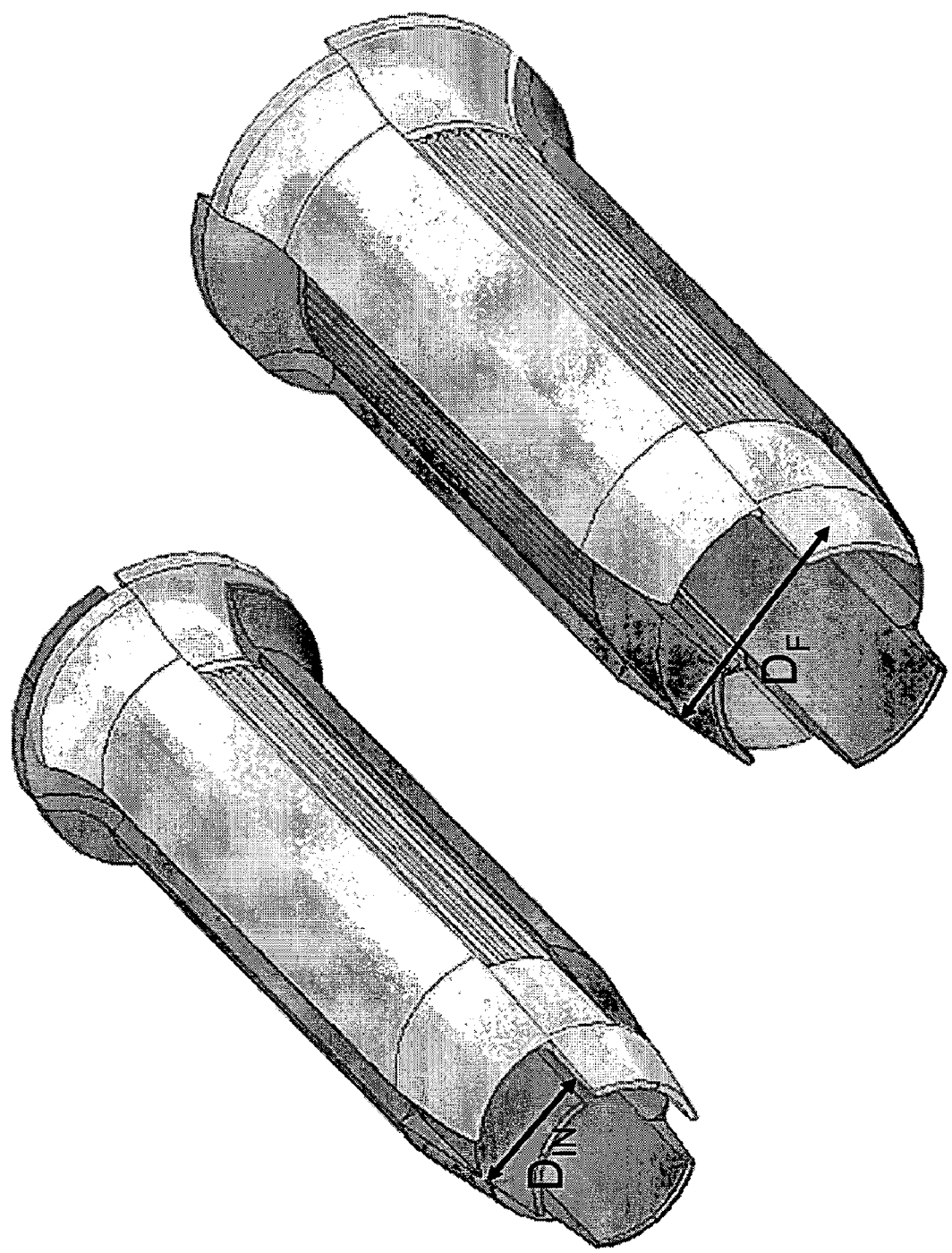
FIG. 3 is a schematic illustration of the hollow tubular member shown in FIG. 2 in different states.

FIGS. 2A, 2B and 3 show the tubular member 21 in more detail. The tubular member 21 has a proximal end 23 of a frustum cone shape, a middle section 25 and a concave distal end 27, the shape of which lowers the risk of hurting the blood vessel. The tubular member has an inner diameter $D_M$ (FIG. 2B) determined so as to fit the blood vessel. The tubular member 21 comprises three overlapping segments 29 and restraining means 20, such as for example a ratchet mechanism or saw tooth mechanism.

As shown in FIG. 3, the tubular member 21 is radially expandable. Consequently, $D_M$ may vary between any desired initial diameter $D_{IN}$ and any desired final diameter $D_F$, i.e. $D_{IN} \leq D_M \leq D_F$. Due to the restraining means 20 the tubular member 21 is prevented from shrinking to any diameter smaller than its current diameter. Therefore, the tubular member 21 can only expand outwardly (i.e. increase its diameter).

During operation, the tubular member 21 is assembled out of its segments 29 over the blood vessel 13, as shown in FIG. 4, while the blood vessel 13 is in its shrunk state and has the diameter $D_{SH}$. Alternatively, the tubular member 21 may be assembled out of its segments 29 prior to the procedure, so that during operation the blood vessel 13 is inserted through the tubular member 21.

The initial diameter $D_{IN}$ of the tubular member 21 is then determined to be at least equal to the shrunk diameter $D_{SH}$ of the blood vessel 13. As shown in FIGS. 5A and 5B, the proximal end 15 of the blood vessel 13 is then everted over the proximal end 23 of the tubular member 21, the frustum cone shape of which facilitates the eversion, so that everted proximal end 14 of the blood vessel 13 tightly surrounds the proximal end 23 of the tubular member 21.

Figure 6B:
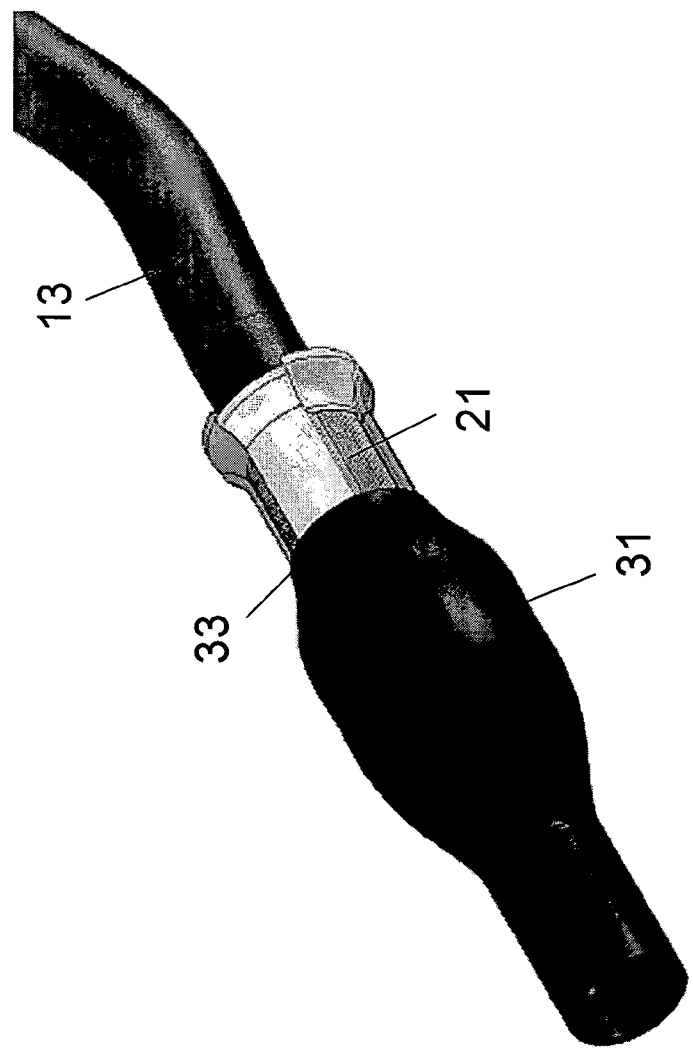
FIGS. 6A and 6B are illustrations a sleeve constituting a part of the device shown in FIG. 1.
Figure 6A:
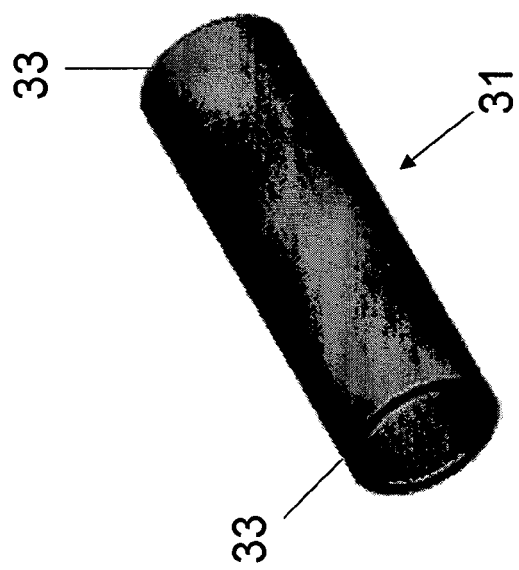

After the proximal ends 15 of the blood vessels 13 are everted over the tubular members 21, as shown in FIGS. 1 and 6B, the elastic sleeve 31 (FIG. 6A) is put over the tubular members 21, first over one everted end 14 and then over the other. The elastic sleeve 31 is long enough to cover both everted ends 14 and at least parts of the middle sections 25 of the tubular members 21, in any diameter $D_M$ that the middle section 25 may have. In this state, portions of the blood vessels 13 proximal to the tubular members 21 still have certain narrowing 17 relative to the diameter $D_B$.

The elastic sleeve 31 holds the blood the everted proximal ends 14 in the everted position. In addition, elastic sleeve 31 maintains the everted proximal ends 14 in any desired, predetermined distance X one from the other (FIG. 1). This may be achieved by stoppers, for example rings, situated within the elastic sleeve 31 and preventing the everted ends 14 from getting closer than the distance X. The stoppers may also be situated within the tubular members 21. The range of the distances X between the everted proximal ends 14 may be in a range of 0 to about 5 mm, more particularly, in a range of about 0.5 mm to about 3 mm, more particularly about 2 mm.

Figure 1B:
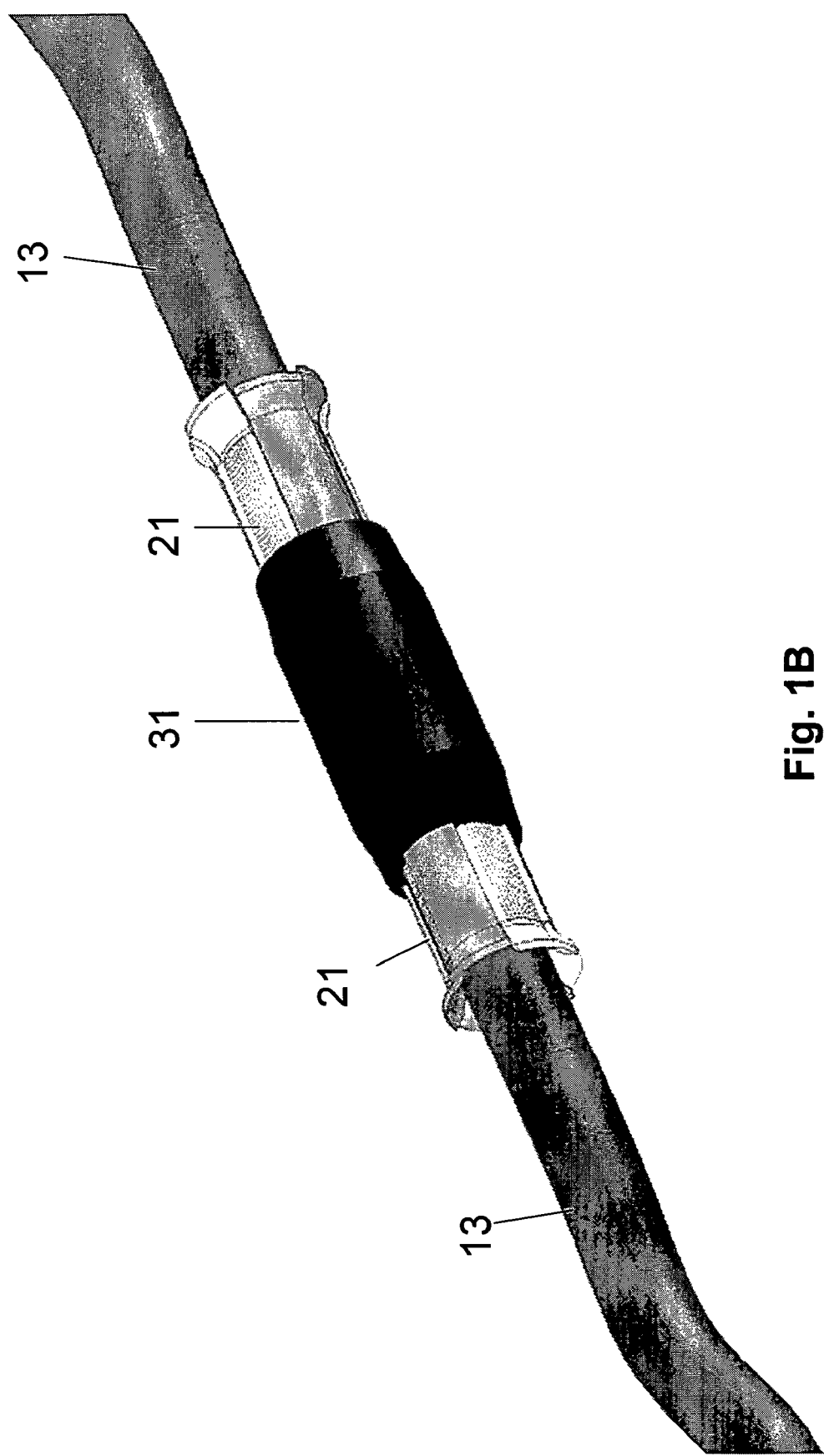

After the procedure described above is over, the blood vessels 13 return to their expanded state, due to the blood flow therethrough, as shown in FIG. 1B. According to the expansion of the blood vessels 13, the tubular members 21 also expand and their expanded diameter $D_F$ corresponds to the expanded diameter $D_{EX}$ of the blood vessels 13, i.e. $D_F \geq D_{EX}$. The expansion of the tubular members 21 may occur as a result of the expansion of the blood vessels 13 or by other means, as will be further described. In this state the blood vessels 13 has a uniform diameter $D_B$ and no narrowing exists on portions thereof.

The dilatation of the blood vessel 13 may be performed by a balloon. In this case, the blood vessel 13 is expanded to at least twice its original diameter. Therefore, the tubular members 21, and consequently the elastic sleeve 31, are adapted to expand at least to the size allowing the insertion and the passage of the inflated balloon through the blood vessel 13. This expandable characteristic permits further increasing of tubular members 21 internal diameter, by means of forced balloon inflation within their lumen.

The device 11 may further be drug eluting, so that each of its components, namely, the tubular members 21 and/or the elastic sleeve 31 may be adapted to release drugs.

All the above described components of the device 11 may be made of inert materials such as silicon, latex, Teflon, Dacron, etc. The components may also be made of absorbent materials, such as polyglactin 910 (Vicryl).

The device 11, though described with reference to the vascular system, may be applicable to other systems of the human body, such as the digestive system or the genitourinary system.

Those skilled in the art to which this invention pertains will readily appreciate that numerous changes, variations, and modifications can be made without departing from the scope of the invention, mutatis mutandis.

The invention claimed is:

1. A device for anastomosis of a first and a second tubular stumps, each having a stump proximal end, and further having a shrunk outer diameter in its shrunk state and an expanded outer diameter in its expanded state, the device comprises:
    a first and a second hollow tubular member, adapted to be placed over said first and second stumps, respectively, each having a tubular member proximal end, a tubular member middle section, a first inner diameter, which is at least equal to said shrunk outer diameter, second inner diameter, which is at least equal to said expanded outer diameter, and a length greater than said second inner diameter, the tubular members further being capable of radially expanding from said first inner diameter to said second inner diameter, each tubular member, while having the first inner diameter, being further adapted to allow everting of the stump proximal end over the tubular member proximal end, wherein the tubular members further comprise restraining means for preventing them from having a diameter less than said first inner diameter, once the tubular members are placed over said stumps; and
    an elastic sleeve having two sleeve ends, adapted to be put on said tubular member proximal ends with the everted ends of said stumps, the sleeve further being adaptable to maintain said everted ends in a predetermined distance.

2. A device according to claim 1, wherein each tubular member comprises at least two segments, each segment partially overlapping with its neighboring segments, to create a diameter at least equal to said first inner diameter.

3. A device according to claim 1, wherein each tubular member is adapted to be expanded due to an expansion of said stumps from said shrunk state to said expanded state.

4. A device according to claim 1, wherein the sleeve is further adapted to cover the everted ends of the stumps and at least a part of the middle sections of the tubular members.

5. A device according to claim 1, wherein said distance is between zero and about 5 mm.

6. A device according to claim 5, wherein said distance is equal to zero.

7. A device according to claim 1, wherein said middle section constitutes a majority of said length.

8. A device according to claim 1, wherein the sleeve is further adapted to cover said everted ends so as to leave exposed portions of the tubular members at least partially constituted of said middle sections.

9. A method of performing an anastomosis of a first and a second tubular stumps, each having a stump proximal end, and further having a shrunk outer diameter in its shrunk state and an expanded outer diameter in its expanded state, the method comprising:
    providing a device comprising a first and a second hollow tubular member, each having a tubular member proximal end, a tubular member middle section, a first inner diameter, which is at least equal to said shrunk outer diameter, second inner diameter, which is at least equal to said expanded outer diameter, and a length greater than said second inner diameter, said tubular members further being capable of radially expanding from said first inner diameter to said second inner diameter; and an elastic sleeve having two sleeve ends;
    determining the first inner diameter of the tubular members;
    placing the first tubular member over the first stump, while it is in its shrunk state;
    placing the second tubular member over the second stump, while it is in its shrunk state;
    everting the proximal ends of the first and second stumps over the proximal ends of the first and second tubular members, respectively;
    putting the sleeve ends on the corresponding proximal ends of the tubular members with the everted proximal ends of the stumps; and
    radially expanding the tubular members from the first inner diameter to the second inner diameter to maintain the everted proximal ends of the stumps in a predetermined distance from each other.

10. A method according to claim 9, further comprising preventing the tubular members from having a diameter less than said first inner diameter, once the tubular member is placed over said stump.

11. A method according to claim 9, further comprising expanding of the tubular members due to an expansion of said stumps from said shrunk state to said expanded state.

12. A method according to claim 9, further comprising maintaining said everted proximal ends of the stumps in said distance by at least one holding means of the sleeve.

13. A method according to claim 9, further comprising covering by the sleeve the everted ends of the stumps and at least a part of the middle sections of the tubular members.

14. A method according to claim 9, further comprising covering said everted ends with said sleeve so as to leave exposed portions of the tubular members at least partially constituted of said middle sections.

* * * * *